US012734286B2

(12) United States Patent
Kuebler et al.

(10) Patent No.: US 12,734,286 B2
(45) Date of Patent: Sep. 15, 2026

(54) OPHTHALMIC SURGICAL DEVICE

(71) Applicant: Carl Zeiss Meditec AG, Jena (DE)

(72) Inventors: Christoph Kuebler, Oberkochen (DE); Philipp Madlinger, Aalen (DE); Susanne Kohlhammer, Blaustein (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/611,455

(22) Filed: Mar. 20, 2024

(65) Prior Publication Data

US 2024/0226411 A1 Jul. 11, 2024

Related U.S. Application Data

(63) Continuation of application No. PCT/EP2022/069879, filed on Jul. 15, 2022.

(30) Foreign Application Priority Data

Sep. 21, 2021 (DE) ..................... 10 2021 210 483.5

(51) Int. Cl.
*A61M 1/00* (2006.01)
*A61F 9/007* (2006.01)

(52) U.S. Cl.
CPC ......... *A61M 1/774* (2021.05); *A61F 9/00763* (2013.01); *A61M 1/60* (2021.05);
(Continued)

(58) Field of Classification Search
CPC .............. A61F 9/00736; A61F 9/00745; A61F 9/00763; A61M 1/60; A61M 1/74;
(Continued)

(56) References Cited

U.S. PATENT DOCUMENTS 5,406,503 A * 4/1995 Williams, Jr. ........ B06B 1/0253 73/579
7,625,388 B2 * 12/2009 Boukhny ............ A61M 3/0216 606/169

(Continued)

FOREIGN PATENT DOCUMENTS

CN 102665621 A 9/2012
DE 20 2012 010 024 U1 3/2013

(Continued)

OTHER PUBLICATIONS

International Preliminary Report on Patentability of the European Patent Office dated Jan. 16, 2023 for international application PCT/EP2022/069879 on which this application is based.

(Continued)

*Primary Examiner* — Quynh-Nhu H. Vu
(74) *Attorney, Agent, or Firm* — Walter Ottesen, P.A.

(57) ABSTRACT

An ophthalmic surgical device includes an irrigation line for irrigation fluid flowing from an irrigation container to a handpiece and an aspiration line for aspiration fluid flowing from the handpiece to a collecting container. A first volumetric flow rate determination apparatus is arranged upstream of the handpiece and determines a first volumetric flow rate in the irrigation line. A second volumetric flow rate determination apparatus is arranged downstream of the handpiece and determines a second volumetric flow rate in the aspiration line. An occlusion determination apparatus acquires a time curve of the first volumetric flow rate and a time curve of the second volumetric flow rate, to compare with stored time curves of the first volumetric flow rate for different occlusion states and stored time curves of the second volumetric flow rate for different occlusion states, and to determine a current occlusion state in the aspiration line therefrom.

11 Claims, 2 Drawing Sheets

(52) U.S. Cl.
CPC ............... *A61M 2205/3334* (2013.01); *A61M 2210/0612* (2013.01)

(58) Field of Classification Search
CPC ............ A61M 1/64; A61M 1/76; A61M 1/77; A61M 1/774; A61M 2205/3334; A61M 2210/0612; A61M 3/022; A61M 3/0216
See application file for complete search history.

(56) References Cited

U.S. PATENT DOCUMENTS

| | | | | |
|---|---|---|---|---|
| 9,144,517 | B2 * | 9/2015 | Kuebler | A61F 9/00745 |
| 10,639,196 | B2 | 5/2020 | Kuebler et al. | |
| 10,722,619 | B2 | 7/2020 | Kuebler et al. | |
| 2010/0241131 | A1 | 9/2010 | Heymann et al. | |
| 2012/0232466 | A1 | 9/2012 | Kuebler et al. | |
| 2015/0196425 | A1 * | 7/2015 | Kuebler | A61M 1/76 604/22 |
| 2017/0216093 | A1 * | 8/2017 | Kuebler | A61M 3/0216 |
| 2019/0060533 | A1 | 2/2019 | Kuebler et al. | |
| 2019/0099546 | A1 * | 4/2019 | Keh | A61M 1/743 |
| 2022/0249283 | A1 | 8/2022 | Kuebler et al. | |
| 2022/0254503 | A1 * | 8/2022 | Kuebler | A61F 9/00736 |

FOREIGN PATENT DOCUMENTS

| | | | | |
|---|---|---|---|---|
| DE | 10 2012 018 983 | A1 | 3/2014 | |
| DE | 10 2015 003 799 | A1 | 9/2016 | |
| DE | 10 2016 201 297 | B3 | 3/2017 | |
| DE | 10 2017 215 677 | B3 | 11/2018 | |
| DE | 10 2019 216 669 | A1 | 4/2021 | |
| DE | 10 2019 216 670 | A1 | 4/2021 | |
| DE | 10 2010 047 012 | A1 | 4/2023 | |
| EP | 2004114 | B1 | 10/2011 | |
| EP | 2 621 423 | B1 | 11/2014 | |
| WO | 2005/092047 | A2 | 10/2005 | |
| WO | 2009036917 | A1 | 3/2009 | |
| WO | 2019069204 | A2 | 4/2019 | |
| WO | WO-2021083938 | A1 * | 5/2021 | A61F 9/00745 |

OTHER PUBLICATIONS

English translation and Written Opinion of the International Searching Authority dated Nov. 8, 2022 for international application PCT/EP2022/069879 on which this application is based.

International Search Report of the European Patent Office dated Nov. 8, 2022 for international application PCT/EP2022/069879 on which this application is based.

English translation and First Office Action of the Chinese Patent Office dated Jun. 21, 2024 for corresponding Chinese patent application 202280064013.8.

Partial English translation and Office Action of the Japanese Patent Office dated Sep. 10, 2024 for corresponding Japanese patent application 2024-518186.

English translation and Second Office Action of the Chinese Patent Office dated Dec. 19, 2024 for corresponding Chinese patent application 202280064013.8.

Partial English translation and Office Action of the Japanese Patent Office dated Feb. 5, 2025 for corresponding Japanese patent application 2024-518186.

Partial English translation and Decision on Rejection of the Chinese Patent Office dated Apr. 22, 2025 for corresponding Chinese patent application 202280064013.8.

* cited by examiner

OPHTHALMIC SURGICAL DEVICE

CROSS-REFERENCE TO RELATED APPLICATIONS

This application is a continuation application of international patent application PCT/EP2022/069879, filed Jul. 15, 2022, designating the United States and claiming priority from German application 10 2021 210 483.5, filed Sep. 21, 2021, and the entire content of both applications is incorporated herein by reference.

BACKGROUND

There are a number of surgical techniques for treating clouding of a crystalline lens, which is referred to in medicine as a cataract. The most widespread technique is phacoemulsification, in which a thin hollow needle is introduced into the crystalline lens and is induced to make ultrasonic vibrations. In its immediate surroundings, the vibrating hollow needle comminutes the lens in such a way that many small lens particles arise, which can be aspirated through a line via a pump. An irrigation fluid (rinsing fluid) is fed during this process via an irrigation fluid line, with the aspiration of the lens particles with the fluid, referred to together as aspiration fluid, taking place through an aspiration fluid line. When the lens has been completely emulsified and removed, a new artificial lens can be inserted into the empty capsular bag, and so a patient treated in this way can recover good vision.

Comminuting the lens using an ultrasonically vibrating hollow needle has proven its worth and works well. However, a fundamental problem consists of the size of the comminuted particles being variable, and such particles being able to clog up the hollow needle in its entrance region. In that case, the aspiration of the aspiration fluid is only possible with difficulties or no longer possible at all. This state is referred to as occlusion. Then, all of the fluid still present in the aspiration fluid line is aspirated, with the result that a significant negative pressure can build up in the case of a correspondingly long-lived occlusion. A dangerous state arises when the particle detaches from the hollow needle again, and aspiration fluid can flow into the hollow needle and the aspiration fluid line again. There is abrupt pressure equalization in the aspiration fluid line on account of the negative pressure, and, in the eye, this may lead to a collapse and to dangerous complications for a patient. US 2022/0254503 describes a relatively complicated ophthalmic surgical control module apparatus.

SUMMARY

It is an object to provide an ophthalmic surgical device which allows an occlusion and the breakup of an occlusion to be identified quickly and reliably.

The object is, for example, achieved by an ophthalmic surgical device which includes:

- an irrigation fluid line through which irrigation fluid can flow from an irrigation fluid container to an ophthalmic surgical handpiece,
- an aspiration fluid line through which aspiration fluid can flow from the ophthalmic surgical handpiece to a collecting container,
- a first volumetric flow rate determination apparatus which is arranged upstream of the handpiece in the flow direction and which is configured to determine a first volumetric flow rate in the irrigation fluid line,
- a second volumetric flow rate determination apparatus which is arranged downstream of the handpiece in the flow direction and which is configured to determine a second volumetric flow rate in the aspiration fluid line,
- an occlusion determination apparatus which is coupled to the first volumetric flow rate determination apparatus and to the second volumetric flow rate determination apparatus and which is configured to acquire the time curve of the first volumetric flow rate and the time curve of the second volumetric flow rate, to respectively carry out a comparison with stored time curves of a first volumetric flow rate in the irrigation fluid line for different occlusion states and stored time curves of a second volumetric flow rate in the aspiration fluid line for different occlusion states, and to determine a current occlusion state in the aspiration fluid line on the basis of the comparisons.

The inventors have observed that knowledge about a volumetric flow rate upstream of the handpiece and downstream of the handpiece is very significant in order to obtain information about an occlusion. In this context, it is advantageous that a volumetric flow rate can be ascertained very quickly, very accurately and with little uncertainty. The inventors have also observed that a conclusion about the intensity present or about a state of an occlusion or a breakup of the occlusion is made possible not only from the absolute magnitude of the volumetric flow rate but also from its time curve. There are typical profiles for a volumetric flow rate in the case of no occlusion, in the case of a partial occlusion, in the case of a complete occlusion, or in the case of any desired situations which can be classified between these states. Such time curves of a first volumetric flow rate and a second volumetric flow rate can be stored in a memory. According to the disclosure, the time curve of a first volumetric flow rate is measured in the irrigation fluid line and compared with previously stored time curves of a first volumetric flow rate in the irrigation fluid line which were ascertained for different occlusion states. This is implemented in the same way for the second volumetric flow rate. According to the disclosure, the time curve of a second volumetric flow rate is measured in the aspiration fluid line and compared with previously stored time curves of a second volumetric flow rate in the aspiration fluid line which were ascertained for different occlusion states. Then, a current occlusion state in the aspiration fluid line can be determined on the basis of these comparisons.

The creation of a correlation between the time curve of an acquired volumetric flow rate and a time curve of a stored volumetric flow rate by way of an occlusion determination apparatus requires only little computational power, and so this can be implemented very quickly. It was found that such a correlation is also very accurate and afflicted by little uncertainty. Hence, the ophthalmic surgical device can be used to quickly and reliably identify whether an occlusion is even present, the intensity with which this occlusion is present, and whether an occlusion is currently breaking up. Thus, the ophthalmic surgical device can be used to quickly and reliably determine a current occlusion state in the aspiration fluid line.

Attention is drawn to the fact that the occlusion determination apparatus acquires both the time curve of the first volumetric flow rate in the irrigation fluid line and the time curve of the second volumetric flow rate in the aspiration fluid line and performs a comparison with both stored time profiles of a first volumetric flow rate in the irrigation fluid line and stored time profiles of a second volumetric flow rate in the aspiration fluid line. A comparison of only a currently acquired time curve of a second volumetric flow rate in the aspiration fluid line with a stored time curve of a second volumetric flow rate in the aspiration fluid line does not suffice for the ascertainment of an occlusion state.

If only such a comparison is performed for a situation in the aspiration fluid line, then it is not possible to identify whether the time curve of the volumetric flow rate in the aspiration fluid line and the time curve of the volumetric flow rate in the irrigation fluid line occur symmetrically to one another. If no symmetry is identifiable in the time curves in the aspiration fluid line and the irrigation fluid line, then this may indicate the presence not of an occlusion but of a different problem. In this context, this can relate to the following problems, this list not being complete:

- a tubing of the irrigation fluid line or the aspiration fluid line has kinked, and so no flow is present;
- the flow in the irrigation fluid line is not sufficiently high owing to the presence of a leak;
- the irrigation fluid container is virtually empty;
- a lens particle is contained in the irrigation fluid line for unknown reasons and leads to an untypical variation in the volumetric flow rate;
- the eye to be treated has a serious injury;
- the size of the puncture for a hollow needle in the cornea is too small, with the result that not enough irrigation fluid can reach into the anterior chamber.

A comparison between the currently acquired time curve of the first volumetric flow rate in the irrigation fluid line with a stored time curve of the first volumetric flow rate in the irrigation fluid line and a comparison between the currently acquired time curve of the second volumetric flow rate in the aspiration fluid line with a stored time curve of the second volumetric flow rate in the aspiration fluid line also includes a check of the symmetry of the time curve of the currently acquired first volumetric flow rate in the irrigation fluid line with the currently acquired time curve of the second volumetric flow rate in the aspiration fluid line.

According to an embodiment, the ophthalmic surgical device includes a control device which is configured to receive an occlusion state signal from the occlusion determination apparatus at an input and to output a control signal for at least one operational parameter of the ophthalmic surgical handpiece to the ophthalmic surgical handpiece at an output.

An occlusion usually occurs right at the start of the aspiration fluid line, that is, still in the ophthalmic surgical handpiece or at the tip of the hollow needle. It is therefore advantageous if knowledge about an occlusion state allows an operational parameter of an ophthalmic surgical handpiece to be controlled such that, for example, the occlusion can break up.

The operational parameter of the ophthalmic surgical handpiece can be an electrical drive power. The electrical drive power can be provided for a longitudinal movement or transverse movement or torsional movement of a piezoceramic of an ophthalmic surgical handpiece for phacoemulsification. The drive power allows for the comminution of a particle, which for example at the tip of a hollow needle clogs up the entrance to the hollow needle, by way of appropriate movement of the hollow needle. The movement can be implemented longitudinally, that is, along a center axis of the hollow needle, or be implemented transversely, that is, across the center axis of the hollow needle, or be implemented by a torsional movement, that is, in a torsional movement around the center axis of the hollow needle. For example, the drive power can be used to drive the hollow needle with a greater lift or travel and thereby provide more energy for the comminution of the particle without changing the frequency.

The electrical drive power can also be provided for a longitudinal movement or transverse movement or torsional movement or rotational movement of a cutting element of a vitrectome. A vitrectome serves to cut for example a vitreous humor and can be clogged up in the region of the cutting tip by particles that are too large, in a manner comparable to a phacoemulsification handpiece. If the onset of an inclusion is identified by way of the ophthalmic surgical device, then the drive power can be used to drive the cutting element at a higher frequency or cutting rate until a normal volumetric flow rate has been re-established.

According to an embodiment of the disclosure, the ophthalmic surgical device includes:

- a first fluid pump which is arranged between the irrigation fluid container and the first volumetric flow rate determination apparatus in the flow direction and which is configured to convey irrigation fluid to the handpiece,
- a second fluid pump which is arranged between the second volumetric flow rate determination apparatus and the collecting container in the flow direction and which is configured to convey aspiration fluid to the collecting container,
- a first timing element which is configured to receive the occlusion state signal at its input, to ascertain as a function of time a first irrigation fluid target pressure depending on the occlusion state signal, and to output a signal for the first irrigation fluid target pressure of the first fluid pump at its output,
- a second timing element which is configured to receive the occlusion state signal at its input, to ascertain as a function of time a first aspiration fluid target pressure depending on the occlusion state signal, and to output a signal for the first aspiration fluid target pressure of the second fluid pump at its output.

As a result, the pressure in the irrigation fluid line can be modified via a first fluid pump and the pressure in the aspiration fluid line can be modified via a second fluid pump. For example, if it is identified that a particle is hanging on the tip of the hollow needle and brings about a complete occlusion in the aspiration fluid line, then the first fluid pump can be controlled such that the pressure in the irrigation fluid line reduces. At the same time, the second fluid pump can be controlled such that the negative pressure in the aspiration fluid line increases very significantly. In this way, an attempt can be made to pull the particle even more strongly against the tip of the hollow needle and possibly break the particle up as a result. In addition, the electrical drive power for the handpiece can also be increased, with the result that the hollow needle is deflected with a greater travel and the particle is broken.

The ophthalmic surgical device may additionally include:

- a first evaluation apparatus which is configured to receive the signal for the first irrigation fluid target pressure at a first input and to receive a signal for a second irrigation fluid target pressure at a second input, and to supply a signal for an irrigation fluid control pressure of the first fluid pump at an output, and
- a second evaluation apparatus which is configured to receive the signal for the first aspiration fluid target pressure at a first input and to receive a signal for a second aspiration fluid target pressure at a second input, and to supply a signal for an aspiration fluid control pressure of the second fluid pump at an output.

The second irrigation fluid target pressure can be provided by a third timing element and the second aspiration fluid target pressure can be provided by a fourth timing element, which are coupled to a foot pedal. By way of an appropriate position of the foot pedal, an operator is able to provide a parameter for the third timing element such that the first evaluation apparatus ascertains an irrigation fluid control pressure, suppliable to the first fluid pump, via the second irrigation fluid target pressure and the first irrigation fluid target pressure. This can be implemented analogously for the aspiration fluid line. By way of an appropriate position of the foot pedal, the operator is able to provide a parameter for the fourth timing element such that the second evaluation apparatus ascertains an aspiration fluid control pressure, suppliable to the second fluid pump, via the second aspiration fluid target pressure and the first aspiration fluid target pressure. For example, careful emulsification of the crystalline lens can be rendered possible as a result.

BRIEF DESCRIPTION OF DRAWINGS

The invention will now be described with reference to the drawings wherein.

DETAILED DESCRIPTION

Figure 1:
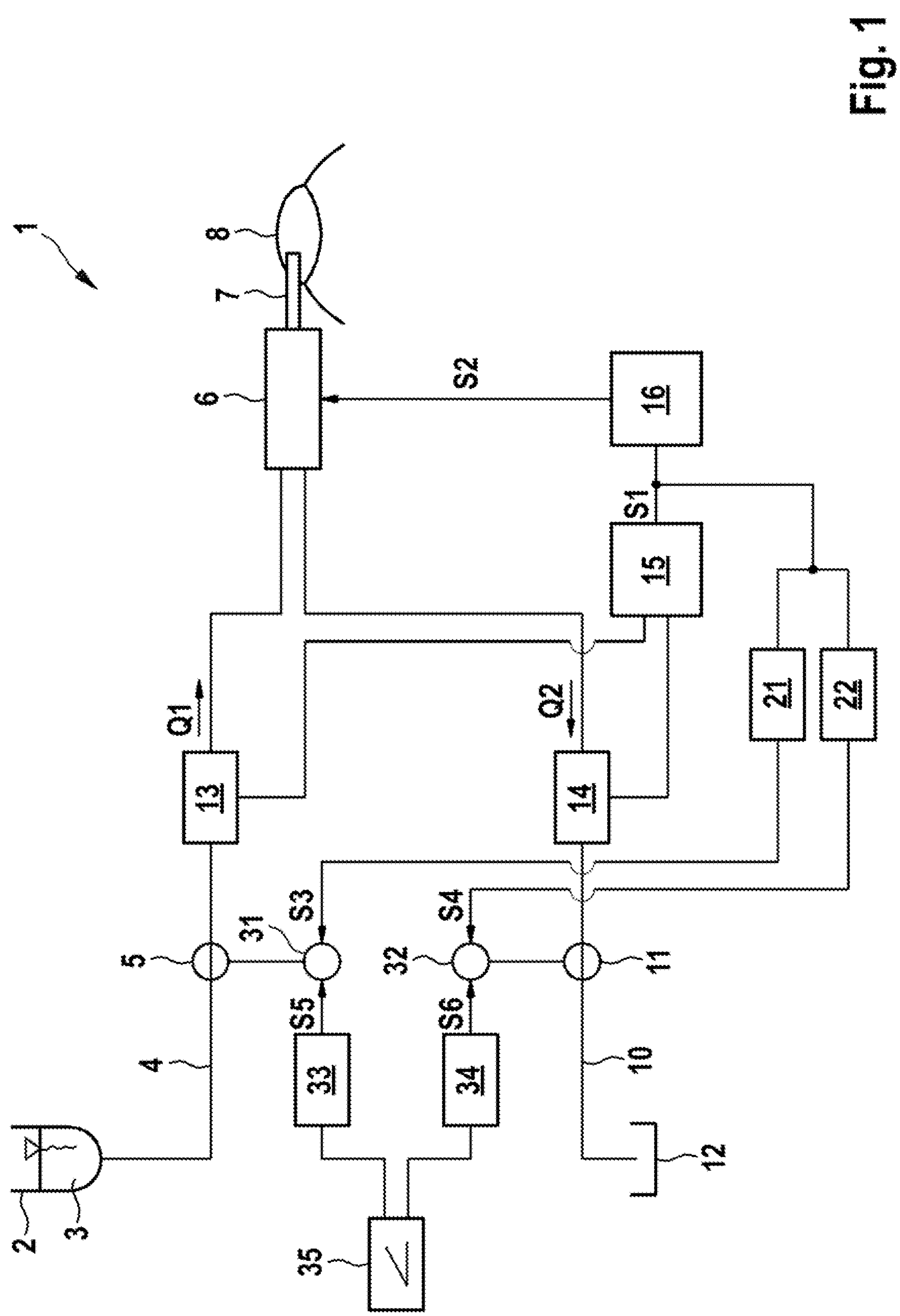
FIG. 1 shows a schematic illustration of an embodiment of an ophthalmic surgical device; and, FIG. 2 shows schematic graphs of pressure curves and volumetric flow rate curves and power supply as a function of time during use of the ophthalmic surgical device.

FIG. 1 shows a schematic illustration of an embodiment of an ophthalmic surgical device 1. An irrigation fluid container 2 contains an irrigation fluid 3 which, through an irrigation fluid line 4 connected to the container, can flow up to an ophthalmic surgical handpiece 6. This can be assisted by a first fluid pump 5 provided in the flow direction between the irrigation fluid container 2 and the handpiece 6. The handpiece 6 may be provided for phacoemulsification and includes a hollow needle 7 which can be inserted into an eye 8 to be treated. Comminuted particles and fluid can flow out of the eye 8 along an aspiration fluid line 10 in the direction of a collecting container 12. This fluid movement is prompted by a second fluid pump 11 which creates a negative pressure in the aspiration fluid line 10.

A first volumetric flow rate determination apparatus 13 which can be used to determine a first volumetric flow rate Q1 in the irrigation fluid line 4 is arranged between the first fluid pump 5 and the handpiece 6 in the flow direction. By preference, the first volumetric flow rate Q1 is determined indirectly by way of the volumetric flow rate determination apparatus 13, for example by virtue of a position of a membrane or a float being detected and the volumetric flow rate being determined therefrom. A second volumetric flow rate determination apparatus 14 which can be used to determine a second volumetric flow rate Q2 in the aspiration line 10 is arranged between the handpiece 6 and the second fluid pump 11 in the flow direction. The second volumetric flow rate is preferably also determined indirectly. The first volumetric flow rate determination apparatus 13 and the second volumetric flow rate determination apparatus 14 are coupled to an occlusion determination apparatus 15 by virtue of the signal from the first volumetric flow rate determination apparatus 13 for the first volumetric flow rate Q1 and the signal from the second volumetric flow rate determination apparatus 14 for the second volumetric flow rate Q2 being transmitted to the occlusion determination apparatus 15.

The occlusion determination apparatus 15 is configured to acquire the time curve of the first volumetric flow rate Q1 and the time curve of the second volumetric flow rate Q2. The occlusion determination apparatus 15 includes a memory element in which time curves of a first volumetric flow rate in the irrigation line and time curves of a second volumetric flow rate in the aspiration line are stored. Each of these stored time curves of a first volumetric flow rate and a second volumetric flow rate is assigned an occlusion state. A comparison between, on the one hand, the time curve of the first volumetric flow rate, acquired via the first volumetric flow rate determination apparatus 13, and the time curve of the second volumetric flow rate, acquired via the second volumetric flow rate determination apparatus 14, and, on the other hand, the stored volumetric flow rates for the irrigation fluid and the aspiration fluid is performed via the occlusion determination apparatus 15. The acquired values and the stored values are correlated with one another, whereupon the occlusion determination apparatus 15 is able to determine an occlusion state.

At its output, the occlusion determination apparatus 15 provides an occlusion state signal S1, which is supplied to an input of a control device 16. The control device 16 processes this occlusion state signal S1 and, at its output, transmits a signal S2 as a control signal for at least one operational parameter of the ophthalmic surgical handpiece 6 to the ophthalmic surgical handpiece 6. The operational parameter can be an electrical power. A phacoemulsification handpiece usually includes piezoceramics as actuators, to which a higher or lower voltage can be applied. This changes the deflection of the piezoceramics and hence the travel or lift of the hollow needle of the handpiece. If the occlusion determination apparatus identifies the presence of an occlusion, then the handpiece can be supplied with a greater power such that a particle clogging up the hollow needle can be comminuted. This likewise applies in the reversed situation: If the breakup of an occlusion is identified, less or no power at all can be supplied to the handpiece since the hollow needle is no longer clogged up by a particle.

According to the embodiment in FIG. 1, the occlusion state signal S1 is also supplied to a first timing element 21 and a second timing element 22. The first timing element 21 is configured to ascertain as a function of time a first irrigation fluid target pressure depending on the occlusion state signal S1 and to provide an associated signal S3 for the first fluid pump 5. For example, if the occlusion determination apparatus 15 identifies the presence of a complete occlusion at the hollow needle of the ophthalmic surgical handpiece 6, the irrigation fluid target pressure can be lowered during a predetermined time period. This prevents additional irrigation fluid from flowing to the eye and increasing the intraocular pressure. At the same time, as a function of time an aspiration fluid target pressure can be ascertained using the second timing element 22 and an associated signal S4 for the second fluid pump 11 can be provided. In the case of a complete occlusion, this may mean that, in a manner comparable to a pulse function, a significantly greater negative pressure is applied immediately in the aspiration fluid line 10 via the second fluid pump 11 in order to hold the particle against the hollow needle tip and break up the particle.

In the embodiment depicted in FIG. 1, the signals S3 and S4 are not supplied directly to the first fluid pump 5 and the second fluid pump 11, respectively. Instead, the signal S3 is supplied to a first input of a first evaluation apparatus 31, which receives a signal S5 from a third timing element 33 at a second input. The third timing element 33 in turn is coupled to a foot operating unit in the form of a foot pedal 35, which can be actuated by a user. In analogous fashion, the signal S4 is supplied to a first input of a second evaluation apparatus 32, which receives a signal S6 from a fourth timing element 34 at a second input. The fourth timing element 34 is coupled to the foot pedal 35. Using this, an operator is able to specify the speed at which the signals S3 and S4 should lead to a change in the irrigation fluid target pressure and aspiration fluid target pressure, whereupon an associated signal for the irrigation fluid control pressure is supplied to the first fluid pump 5 at an output of the first evaluation apparatus 31 and an associated signal for the aspiration fluid control pressure is supplied to the second fluid pump 11 at an output of the second evaluation apparatus 32.

It is important that the ophthalmic surgical device according to the disclosure only supplies power to an ophthalmic surgical handpiece 6 if an occlusion is identified. As a result of the comparison of stored time curves of an irrigation fluid volumetric flow rate and aspiration fluid volumetric flow rate with a currently acquired time curve of irrigation fluid and aspiration fluid, it is possible to supply only a minimally required power. This significantly reduces the risk of overheating, for example in the region where the hollow needle punctures the cornea, and hence burning of the cornea. The ophthalmic surgical device according to the disclosure thus reduces the risk of medical complications and increases the safety of an ophthalmic surgical procedure.

Figure 2:
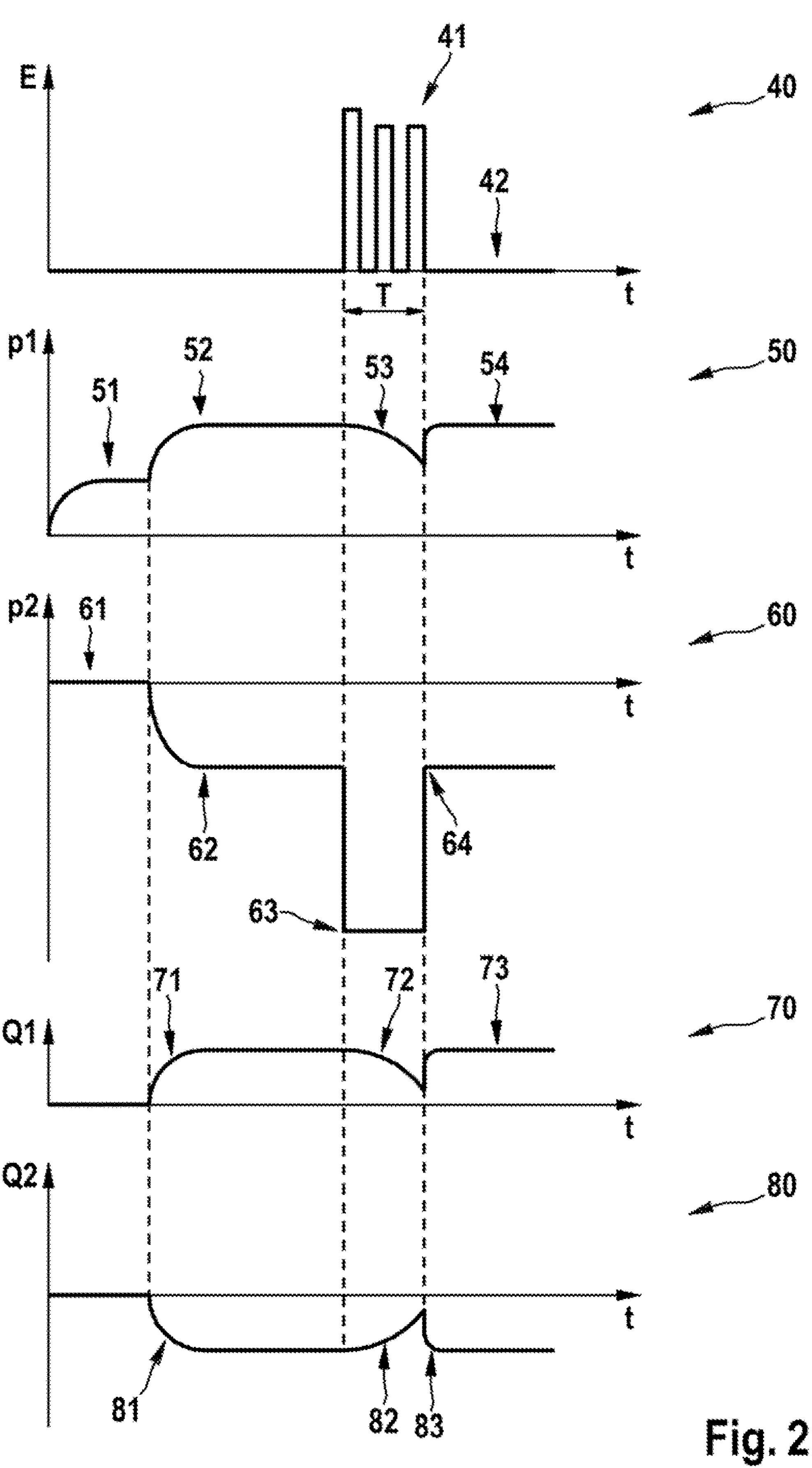

FIG. 2 depicts a few graphs of operational variables as a function of time t. The graph 40 shows a curve of energy pulses, the graph 50 shows a curve of an irrigation fluid pressure p1 in an irrigation fluid line, graph 60 shows a curve of an aspiration fluid pressure p2 in an aspiration fluid line, graph 70 shows a curve of a first volumetric flow rate Q1 in an irrigation fluid line, and graph 80 shows a curve of a second volumetric flow rate Q2 in an aspiration fluid line.

The curves are each explained using reference signs below. If an irrigation fluid flows in an irrigation fluid line at the outset, then a first pressure is prevalent in the irrigation fluid line; see reference sign 51. At this instant, negative pressure is not yet present in the aspiration fluid line; see 61. There is an increase of the first volumetric flow rate Q1 in the irrigation fluid line if the first fluid pump 5 then conveys the irrigation fluid; see 71. At the same time, the second fluid pump 11 is put into operation such that the second volumetric flow rate Q2 in the aspiration fluid line increases; see 81. The irrigation fluid pressure increases in the irrigation fluid line—see 52—and the negative pressure increases in the aspiration fluid line; see 62. The values for the irrigation fluid pressure, the aspiration fluid pressure, the first volumetric flow rate and the second volumetric flow rate remain at their level if there is no occlusion. However, upon onset of an occlusion there is a reduction of the second volumetric flow rate in the aspiration line—see 82—and a reduction of the first volumetric flow rate in the irrigation fluid line; see 72. It is easy to see that this reduction of the volumetric flow rates occurs symmetrically with respect to one another. This is identified via the occlusion determination apparatus 15, whereupon the second fluid pump 11 is driven to bring about a relatively strong negative pressure in the aspiration line; see 63. The second fluid pump 11 is preferably a membrane pump to allow it to react so quickly. This also applies to the first fluid pump 5, which is preferably a membrane pump. The membrane pump can be constructed as described in US 2017/0216093.

The occlusion determination apparatus 15 is also coupled to the control device 16. The control device 16 transmits a control signal for an operational parameter, for example the electrical power, to the ophthalmic surgical handpiece 6. In this example, a handpiece for phacoemulsification is assumed, with the handpiece being controlled by energy pulses; see 41. The energy pulses may decrease, remain constant or increase over time, with the result that the graph in FIG. 2 represents only an example. It is also possible to modify the ratio between pulse duration and pulse pause (duty cycle), and the cutting rate can be modified in the case of a vitrectome. In addition, the first fluid pump 5 is driven such that the pressure p1 in the irrigation fluid line decreases; see 53.

In the example, an assumption is made that the particle at the tip of the hollow needle 7 of the handpiece 6 breaks up into smaller pieces on account of the applied energy pulses 41 and the large negative pressure p2 in the aspiration fluid line, and the occlusion thus ends. When the negative pressure in the aspiration fluid line is still large, the second volumetric flow rate increases quickly again—see 83—and the first volumetric flow rate in the irrigation line also increases quickly again; see 73. This is identified by the occlusion determination apparatus 15. Thereupon, the second fluid pump 11 is driven such that the large negative pressure is reduced immediately; see 64. At the same time, the energy pulses are terminated immediately; see 42. In addition, the first fluid pump 5 is driven such that a previously applied pressure is attained again in the irrigation line; see 54.

Attention is drawn to the fact that only the first volumetric flow rate Q1 and the second volumetric flow rate Q2 are determined. The respective pressure p1 in the irrigation line 4 and pressure p2 in the aspiration line 10 are not determined. The pressure curves shown in graphs 50 and 60 are only depicted for explanatory purposes, but are not measured by the ophthalmic surgical device.

If the ophthalmic surgical handpiece is a vitrectome, the operational parameter for the vitrectome can be the electrical power for a cutting rate. Thus, the power can be used to operate the cutting element at a higher frequency. In graph 40, the cutting rate, rather than energy pulses, can then be significantly higher during the time period T than during the time periods therebefore and thereafter.

It is understood that the foregoing description is that of the preferred embodiments of the invention and that various changes and modifications may be made thereto without departing from the spirit and scope of the invention as defined in the appended claims.

REFERENCE SIGNS

1 Ophthalmic surgical device
2 Irrigation fluid container
3 Irrigation fluid
4 Irrigation fluid line
5 First fluid pump
6 Ophthalmic surgical handpiece
7 Hollow needle
8 Eye
10 Aspiration fluid line
11 Second fluid pump
12 Collecting container
13 First volumetric flow rate determination apparatus

14 Second volumetric flow rate determination apparatus
15 Occlusion determination apparatus
16 Control device
21 First timing element
22 Second timing element
31 First evaluation apparatus
32 Second evaluation apparatus
33 Third timing element
34 Fourth timing element
35 Foot pedal
40, 50, 60, 70, 80 Graphs
41, 42, 51-54, 61-64, 71-73, 81-83 Operational states in graphs 40, 50, 60, 70, 80
p1 Irrigation fluid pressure
p2 Aspiration fluid pressure
Q1 First volumetric flow rate
Q2 Second volumetric flow rate
S1 Occlusion state signal
S2 Control signal for the handpiece
S3 Signal for the first irrigation fluid target pressure
S4 Signal for the first aspiration fluid target pressure
S5 Signal for the second irrigation fluid target pressure
S6 Signal for the second aspiration fluid target pressure
T Time period of the occlusion

The invention claimed is:

1. An ophthalmic surgical device comprising:

an irrigation fluid line configured to have irrigation fluid flow therethrough from an irrigation fluid container to an ophthalmic surgical handpiece;

an aspiration fluid line configured to have aspiration fluid flow therethrough from the ophthalmic surgical handpiece to a collecting container;

a first volumetric flow meter, wherein the first volumetric flow meter is positioned upstream of the ophthalmic surgical handpiece in a flow direction, and wherein the first volumetric flow meter is configured to determine a first volumetric flow rate in the irrigation fluid line;

a second volumetric flow meter, wherein the second volumetric flow meter is positioned downstream of the ophthalmic surgical handpiece in the flow direction, and wherein the second volumetric flow meter is configured to determine a second volumetric flow rate in the aspiration fluid line; and an occlusion determination apparatus coupled to the first volumetric flow meter and to the second volumetric flow meter;

wherein the occlusion determination apparatus is configured to acquire a time curve of the first volumetric flow rate and a time curve of the second volumetric flow rate, wherein the occlusion determination apparatus quantitates a difference between the time curve of the first volumetric flow rate and the time curve of the second volumetric flow rate and one or more stored standard time curves of the first volumetric flow rate in the irrigation fluid line and of the second volumetric flow rate in the aspiration fluid line for respectively different known occlusion states, thereby detecting an occlusion state in the aspiration fluid line based on symmetry or correlation of the time curve of the first volumetric flow rate and the time curve of the second volumetric flow rate to the one or more stored standard time curves, wherein the occlusion states comprise: a state of no occlusion, a state of partial occlusion, and a state of complete occlusion.

2. The ophthalmic surgical device of claim 1, further comprising:

a control device configured to receive an occlusion state signal from the occlusion determination apparatus at an input, and wherein the control device sends a control signal for at least one operational parameter of the ophthalmic surgical handpiece to the ophthalmic surgical handpiece at an output.

3. The ophthalmic surgical device of claim 2, wherein the at least one operational parameter of the ophthalmic surgical handpiece is an electrical drive power.

4. The ophthalmic surgical device of claim 3, wherein the electrical drive power provides a longitudinal movement, transverse movement, or torsional movement of a piezoceramic of the ophthalmic surgical handpiece for phacoemulsification.

5. The ophthalmic surgical device of claim 3, wherein the electrical drive power provides a longitudinal movement, transverse movement, torsional movement, or rotational movement of a cutting element of a vitrectome.

6. The ophthalmic surgical device of claim 2, further comprising:

a first fluid pump, wherein the first fluid pump is positioned between the irrigation fluid container and the first volumetric flow meter in the flow direction, and wherein the first fluid pump is configured to convey irrigation fluid to the ophthalmic surgical handpiece;

a second fluid pump, wherein the second fluid pump is positioned between the second volumetric flow meter and the collecting container in the flow direction, and wherein the second fluid pump is configured to convey aspiration fluid to the collecting container;

a first timing element, wherein the first timing element is configured to receive the occlusion state signal at a first timing element input, wherein the first timing element is configured to ascertain as a function of time a first irrigation fluid target pressure depending on the occlusion state signal, and wherein the first timing element is configured to output a signal for the first irrigation fluid target pressure of the first fluid pump at a first timing element output; and, a second timing element, wherein the second timing element is configured to receive the occlusion state signal at a second timing element input, wherein the second timing element determines, as a function of time, a first aspiration fluid target pressure depending on the occlusion state signal, and wherein the second timing element emits a signal for the first aspiration fluid target pressure of the second fluid pump at a second timing element output.

7. The ophthalmic surgical device of claim 6, further comprising:

a first evaluation apparatus, wherein the first evaluation apparatus is configured to receive the occlusion state signal for the first irrigation fluid target pressure at a first input, wherein the first evaluation apparatus is configured to receive a signal for a second irrigation fluid target pressure at a second input, and wherein the first evaluation apparatus is configured to supply a signal for an irrigation fluid control pressure of the first fluid pump at a first evaluation apparatus output; and, a second evaluation apparatus, wherein the second evaluation apparatus is configured to receive the signal for the first aspiration fluid target pressure at a first input, wherein the second evaluation apparatus is configured to receive a signal for a second aspiration fluid target pressure at a second input, and wherein the second evaluation apparatus is configured to supply a signal for an aspiration fluid control pressure of the second fluid pump at an output.

8. An ophthalmic surgical device comprising:

an irrigation fluid line configured to have irrigation fluid flow therethrough from an irrigation fluid container to an ophthalmic surgical handpiece;

an aspiration fluid line configured to have aspiration fluid flow therethrough from the ophthalmic surgical handpiece to a collecting container;

a first volumetric flow arranged meter, wherein the first volumetric flow meter is positioned upstream of the ophthalmic surgical handpiece in a flow direction, and wherein the first volumetric flow meter is configured to determine a first volumetric flow rate in the irrigation fluid line;

a second volumetric flow arranged meter, wherein the second volumetric flow meter is positioned downstream of the ophthalmic surgical handpiece in the flow direction, and wherein the second volumetric flow meter is configured to determine a second volumetric flow rate in the aspiration fluid line;

an occlusion determination apparatus coupled to the first volumetric flow meter and to the second volumetric flow meter;

wherein the occlusion determination apparatus is configured to acquire a time curve of the first volumetric flow rate and a time curve of the second volumetric flow rate, wherein the occlusion determination apparatus quantitates a difference between the time curve of the first volumetric flow rate and the time curve of the second volumetric flow rate and one or more stored standard time curves of the first volumetric flow rate in the irrigation fluid line and of the second volumetric flow rate in the aspiration fluid line for respectively different known occlusion states, thereby detecting an occlusion state in the aspiration fluid line based on symmetry or correlation of the time curve of the first volumetric flow rate and the time curve of the second volumetric flow rate to the one or more stored standard time curves;

a control device, wherein the control device is configured to receive an occlusion state signal from the occlusion determination apparatus at a control device input, and wherein the control device is configured to output a control signal for at least one operational parameter of the ophthalmic surgical handpiece to the ophthalmic surgical handpiece at a control device output;

a first fluid pump, wherein the first fluid pump is positioned between the irrigation fluid container and the first volumetric flow meter in the flow direction, and wherein the first fluid pump is configured to convey irrigation fluid to the ophthalmic surgical handpiece;

a second fluid pump, wherein the second fluid pump is positioned between the second volumetric flow meter and the collecting container in the flow direction, and wherein the second fluid pump is configured to convey aspiration fluid to the collecting container;

a first timing element, wherein the first timing element is configured to receive the occlusion state signal at a first timing element input, wherein the first timing element is configured to ascertain as a function of time a first irrigation fluid target pressure depending on the occlusion state signal, and wherein the first timing element is configured to output a signal for the first irrigation fluid target pressure of the first fluid pump at a first timing element output;

a second timing element, wherein the second timing element is configured to receive the occlusion state signal at a second timing element input, wherein the second timing element is configured to ascertain, as a function of time, a first aspiration fluid target pressure depending on the occlusion state signal, and wherein the second timing element is configured to output a signal for the first aspiration fluid target pressure of the second fluid pump at a second timing element output;

a first evaluation apparatus, wherein the first evaluation apparatus is configured to receive the signal for the first irrigation fluid target pressure at a first input, wherein the first evaluation apparatus is configured to receive a signal for a second irrigation fluid target pressure at a second input, and wherein the first evaluation apparatus is configured to supply a signal for an irrigation fluid control pressure of the first fluid pump at a first evaluation apparatus output;

a second evaluation apparatus wherein the second evaluation apparatus is configured to receive the signal for the first aspiration fluid target pressure at a first input, wherein the second evaluation apparatus is configured to receive a signal for a second aspiration fluid target pressure at a second input, and wherein the first evaluation apparatus is configured to supply a signal for an aspiration fluid control pressure of the second fluid pump at an output;

third and fourth timers connected to said first and second evaluation devices, respectively, wherein the third and fourth timers supply corresponding ones of said fluid target pressures; and, a foot operated unit connected to said third and fourth timers and configured to specify the speed at which a change in-the irrigation fluid target pressure and the aspiration fluid target pressure should occur.

9. The ophthalmic surgical device of claim 8, wherein the at least one operational parameter of the ophthalmic surgical handpiece is an electrical drive power.

10. The ophthalmic surgical device of claim 9, wherein the electrical drive power provides a longitudinal movement, transverse movement, or torsional movement of a piezoceramic of the ophthalmic surgical handpiece for phacoemulsification.

11. The ophthalmic surgical device of claim 9, wherein the electrical drive power provides a longitudinal movement, transverse movement, torsional movement, or rotational movement of a cutting element of a vitrectome.

* * * * *